(12) United States Patent
Leschinsky et al.

(10) Patent No.: US 12,128,261 B2
(45) Date of Patent: Oct. 29, 2024

(54) WEARABLE AIR STERILIZER FOR EVERYDAY USE DURING COVID-19 AND IN A POST-PANDEMIC PERIOD

(71) Applicants: Gary A Leschinsky, Mahwah, NJ (US); Barbara D Leschinsky, Mahwah, NJ (US); Mark D Leschinsky, Mahwah, NJ (US)

(72) Inventors: Gary A Leschinsky, Mahwah, NJ (US); Barbara D Leschinsky, Mahwah, NJ (US); Mark D Leschinsky, Mahwah, NJ (US)

( * ) Notice: Subject to any disclaimer, the term of this patent is extended or adjusted under 35 U.S.C. 154(b) by 732 days.

(21) Appl. No.: 17/317,113

(22) Filed: May 11, 2021

(65) Prior Publication Data

US 2021/0353969 A1 Nov. 18, 2021

Related U.S. Application Data

(60) Provisional application No. 63/075,288, filed on Sep. 7, 2020, provisional application No. 63/025,377, filed on May 15, 2020.

(51) Int. Cl.

| | | |
|---|---|---|
| *A42B 7/00* | (2006.01) |
| *A42B 1/24* | (2021.01) |
| *A61L 9/20* | (2006.01) |
| *A62B 7/00* | (2006.01) |
| *A62B 9/00* | (2006.01) |
| *A62B 18/00* | (2006.01) |
| *A62B 18/08* | (2006.01) |
| *A42B 3/28* | (2006.01) |
| *H04M 1/725* | (2021.01) |

(52) U.S. Cl.
CPC .................. *A62B 7/00* (2013.01); *A42B 1/24* (2013.01); *A61L 9/20* (2013.01); *A62B 9/00* (2013.01); *A62B 18/003* (2013.01); *A62B 18/006* (2013.01); *A62B 18/08* (2013.01); *A62B 18/084* (2013.01); *A42B 3/286* (2013.01); *A61L 2209/11* (2013.01); *A61L 2209/12* (2013.01); *A61L 2209/15* (2013.01); *H04M 1/725* (2013.01)

(58) Field of Classification Search
CPC .................................... A62B 7/00; A42B 1/24
See application file for complete search history.

(56) References Cited

U.S. PATENT DOCUMENTS

| | | |
|---|---|---|
| 432,728 A | 7/1890 | Eliel |
| 1,443,475 A | 1/1923 | Karus |
| 2,500,982 A | 3/1950 | Fligel |
| 3,168,748 A | 2/1965 | Limberg |
| 3,353,191 A | 11/1967 | Dahly |
| 3,683,907 A | 9/1972 | Cotabish |

(Continued)

FOREIGN PATENT DOCUMENTS

| | | |
|---|---|---|
| WO | WO9908752 | 2/1999 |
| WO | WO2006135231 | 12/2006 |

*Primary Examiner* — Kevin Joyner
(74) *Attorney, Agent, or Firm* — Boris Leschinsky

(57) ABSTRACT

A wearable air sterilizer features an air disinfection chamber and a slidable face shield mounted on a headwear item such as a conventional baseball cap. The air disinfection chamber features one or more LEDs emanating ultraviolet light at a germicidal wavelength to inactivate airborne pathogens in the passing air and provide the user with a personalized air supply free from COVID-19 and other viruses.

20 Claims, 11 Drawing Sheets

(56) References Cited

U.S. PATENT DOCUMENTS

| | | | |
|---|---|---|---|
| 3,736,927 A | 6/1973 | Misaqi | |
| 3,881,198 A | 5/1975 | Waters | |
| 3,881,478 A | 5/1975 | Rosendahl | |
| 3,963,021 A | 6/1976 | Bancroft | |
| 4,280,491 A | 7/1981 | Berg | |
| 4,546,496 A | 10/1985 | Lewis | |
| 4,980,928 A | 1/1991 | Ellis | |
| 5,035,004 A | 7/1991 | Koester | |
| 5,048,516 A | 9/1991 | Soderberg | |
| 5,054,479 A | 10/1991 | Yelland | |
| 5,085,231 A | 2/1992 | Johnson | |
| 5,153,943 A | 10/1992 | Clement | |
| 5,165,395 A | 11/1992 | Ricci | |
| 5,533,500 A | 7/1996 | Her-Mou | |
| 5,623,732 A | 4/1997 | Olajide | |
| 5,694,647 A | 12/1997 | Crickmore | |
| 5,875,493 A | 3/1999 | MacDonald | |
| 6,752,146 B1 | 6/2004 | Altshuler | |
| 6,772,762 B2 | 9/2004 | Piesinger | |
| 6,789,268 B2 | 9/2004 | Yan | |
| 6,990,691 B2 | 1/2006 | Klotz | |
| 6,996,852 B1 | 2/2006 | Cabrera | |
| 7,036,502 B2 | 5/2006 | Manne | |
| 7,051,732 B2 | 5/2006 | Uusitalo | |
| 7,118,608 B2 | 10/2006 | Lovell | |
| 7,143,451 B2 | 12/2006 | Lundgren | |
| D599,533 S | 9/2009 | Yun | |
| 8,024,818 B1 | 9/2011 | Davenport | |
| 8,051,497 B1 | 11/2011 | Erhardt | |
| 8,733,356 B1 | 5/2014 | Roth | |
| 8,960,190 B2 | 2/2015 | James | |
| 9,155,923 B2 | 10/2015 | Proctor | |
| 9,248,248 B2 | 2/2016 | Virr | |
| 9,380,822 B2 | 7/2016 | Foster | |
| 9,439,466 B2 | 9/2016 | Woo | |
| 10,335,618 B2 | 7/2019 | Zhou | |
| 10,448,685 B2 | 10/2019 | Czajka | |
| 2004/0055601 A1 | 3/2004 | De Luca | |
| 2005/0061316 A1 | 3/2005 | Manne | |
| 2005/0284470 A1 | 12/2005 | Wei | |
| 2006/0213523 A1 | 9/2006 | VanDerWoude | |
| 2007/0050898 A1 | 3/2007 | Larson | |
| 2007/0275651 A1* | 11/2007 | Palmer | F24F 8/192 454/238 |
| 2009/0004047 A1 | 1/2009 | Hunter | |
| 2009/0025716 A1 | 1/2009 | Glazman | |
| 2010/0224194 A1 | 9/2010 | Walker | |
| 2013/0118506 A1 | 5/2013 | Osipov | |
| 2013/0139289 A1 | 6/2013 | Booth Jackson | |
| 2013/0152919 A1 | 6/2013 | Billingsley | |
| 2015/0090254 A1 | 4/2015 | Pavalarajan | |
| 2016/0066643 A1 | 3/2016 | Squair | |
| 2016/0339192 A1 | 11/2016 | Lee | |
| 2017/0361133 A1 | 12/2017 | Yu | |
| 2021/0339061 A1* | 11/2021 | Fajardo | A62B 18/08 |
| 2022/0202982 A1* | 6/2022 | Fulbrook | A62B 18/02 |
| 2023/0173117 A1* | 6/2023 | Tung | A41D 13/1184 128/858 |

\* cited by examiner

WEARABLE AIR STERILIZER FOR EVERYDAY USE DURING COVID-19 AND IN A POST-PANDEMIC PERIOD

CROSS-REFERENCE DATA

This US patent application claims a priority date benefit of the U.S. Provisional Patent Application No. 63/025,377 entitled "No-mask staged respirator and face covering for everyday use in COVID-19-affected areas" filed 15 May 2020 and the U.S. Provisional Patent Application No. 63/075,288 entitled "A wearable air sterilizer for everyday us in COVID-19-affected areas" filed 7 Sep. 2020, both documents are incorporated herein by reference in their respective entireties.

BACKGROUND

Without limiting the scope of the invention, its background is described in connection with portable powered air sterilizers. More particularly, the invention describes a wearable air sterilizer having multiple modes of use and stages of protection, wherein the air sterilizer may be configured to rapidly switch to a desired mode of operation depending on surrounding circumstances.

For the purposes of this description, the terms "coronavirus", "COVID-19", "SARS-CoV-2" are used interchangeably and generally refer to an airborne virus that can infect a human being with COVID-19. Although the present invention is intended primarily for the prevention of the COVID-19 by inactivation of the SARS-CoV-2 virus and uses that term in describing the technology aimed to disinfect the air containing that virus, these terms are used broadly to include other airborne pathogens, that can be destroyed using disinfection techniques described below, such as influenza viruses, adenoviruses, tuberculosis, measles, chickenpox, etc. The term "airborne pathogen" is used to broadly describe a variety of viruses, fungi, bacteria, and other harmful microorganisms that can be suspended in the air, transmitted through the air, and cause a variety of illnesses and diseases in humans and animals.

The terms "sterilization", "sterilizer", "disinfection", "disablement", and "inactivation" are also used interchangeably to define a sufficient reduction of a viable airborne pathogen load in the air mass so as to prevent or at least significantly reduce the risk of contracting the disease caused by that airborne pathogen when inhaled by the user.

The onset of the coronavirus pandemic in early 2020 caused an unprecedented loss of human lives, human suffering, and economic collapse. Measures to protect individuals from contracting the disease are in high demand. Three main pathways of SARS-CoV-2 virus transmission have been identified:

a. Through "fomites", or objects that have surfaces contaminated with the virus, including human skin. Frequent handwashing and using hand sanitizers have been recommended. Recently, however, the CDC (Centers for Disease Control and Prevention) stated that fomites are a possible pathway of transmission but likely not that is major;

b. Through droplets, or small bits of saliva or respiratory fluid that affected individuals expel when they cough, sneeze or talk. Droplets—which WHO (World Health Organization) and CDC maintain is the primary pathway of Covid-19 transmission—are propelled through the air but fall to the ground after traveling 3-6 feet. This notion prompted a recommendation for maintaining social distancing of at least 6 ft; and finally c. Aerosol transmission, which is similar to droplet transmission, except that the bits of fluid are so small (less than about 50 microns) that they linger in the air for minutes to hours. Research shows that this is likely the main pathway for Covid-19 transmission, especially indoors and in poor ventilated areas where many people may stay for extended periods of time (reference is made to Jose-Luis Jimenez. Covid-19 is transmitted through aerosols. We have enough evidence, now it is time to act. Time Magazine. Aug. 25, 2020). Another detriment of aerosols is that they penetrate deeper into the lungs of a person where immunity defenses are reduced as compared with upper respiratory tract defenses, which may explain why some people are getting more sick than others.

Covid-19 imposed major restrictions on people living in the affected areas. Temporary lockdowns, mandates for social distancing, and face covering are now commonplace in the US and throughout the world. The most common form of a face covering is a face mask—see FIG. 1A. Depending on the specifics of regional and local regulations, a face mask is required to be used by everyone when outside the home, such as shopping, walking on the streets, attending schools, and in many other situations when interacting with other people may be encountered.

While a face mask is suitable for use by medical professionals for a limited time and typically in a particular singular setting, it is not an ideal face covering for prolonged use in a variety of everyday situations. The following limitations of face masks limit their utility for everyday use:

Many consumers are not as well educated as medical professionals and may not understand or be willing to size or fit the mask properly on their faces. It is common to see people wearing their masks under their noses, making the mask ineffective. Removal of a used mask is not even discussed or taught, let alone properly practiced;

Facial hair such as a beard makes the mask ineffective as it does not seal around the edge of its periphery to face skin;

When fitted properly, the face mask makes breathing more difficult as every time the person inhales fresh air, it must go through a filter material of the mask, which has a noticeable level of airflow resistance;

Exhaling into space under the face mask makes the surrounding skin moist and hot, making the wearer of the mask uncomfortable;

Fogging of glasses is a common complaint when wearing a mask.

Presumably, the mask needs to be replaced after every single use or at least based on a limited number of hours of use. CDC recommends the replacement of N95 masks every 8 hours. In reality, many consumers reuse the same mask for many days;

Disinfection and reuse of the masks are not recommended. Even when done properly, it is a complex and tedious procedure that is rarely followed by a layperson;

It is impossible to eat or drink when wearing a face mask, so it cannot be used in restaurants or other dining places;

Speech sounds are muffled when wearing a mask, making it difficult to communicate with others, especially while talking on a telephone;

A face mask does not protect the eyes or other non-covered parts of the face and the head of the user;

Finally, the mask covers the face to a large extent making it impossible to see the person fully. That makes many people uncomfortable to communicate with a mask-wearing person as they cannot read the facial expressions of that person, see the person smiling or speaking with them.

Better personal protective equipment (PPE) is therefore needed to address the disadvantages of a face mask described above.

The next step-up from a face mask is PAPR, which stands for a Powered Air-Purifying Respirator—see FIG. 1B. A typical PAPR is a bulky piece of medical equipment including a rigid and heavy helmet mounted on top of a wearer's head, a full face shield affixed to the helmet and surrounding the face of the user, a cover for complete isolation of the rest of the user's head from the outside environment, and a corrugated hose descending typically from the back of the helmet to a belt-mounted battery-powered air processing unit, where a heavy blower pushes the ambient air through one or more filters to remove all possible contaminants from the air—before infusing the air into the space of the helmet to create a positive pressure purified local atmosphere for the user to breathe.

PAPRs are certainly highly effective in providing pure air for the user. They also feature a clear face shield so the person inside can see better and can be seen by others. They are, however, heavy, bulky, esthetically unattractive—and, therefore are not suitable or even practical for everyday use.

The need, therefore, exists for a lightweight PPE that provides adequate protection against COVID-19 and allows for extended use with improved comfort.

High-risk patients are at an increased risk to suffer devastating consequences when contracting COVID-19. These patients include the elderly and people with a variety of preexisting conditions and chronic illnesses. In particular, immunocompromised patients find themselves in double jeopardy when it comes to COVID-19:

on the one side, their suppressed immune system may not respond adequately to a vaccine to produce sufficient protection—putting them at a higher risk of contracting the disease;

and on the other side, they are more likely to develop a severe form of the disease due to their underlying conditions.

Chemotherapy, radiation, and other common cancer treatments are known to reduce the immune response in these patients, putting them at a higher risk for COVID-19. In addition to cancer patients, there is a broad range of other high-risk patients including many elderly, diabetics, transplant recipients, and patients with other comorbidities. A study by the Johns Hopkins University shows that only 17% of transplant recipients had detectable levels of COVID-19 antibodies 20 days after the first dose of a messenger RNA vaccine (www.jama.com, published online Mar. 15, 2021), a much lower vaccine response than the general population.

Similarly, many patients suffering from rheumatic and musculoskeletal diseases have a reduced response to COVID-19 vaccines. One study showed that only 74% of these patients had detectable antibodies after vaccination, including a very low 27.3% vaccine responders in patients taking mycophenolate as an immunosuppression medication (Boyarsky et al, *Ann Rheum Dis,* 2021). With about 5% of the general population (and a higher proportion of the elderly) suffering from reduced immune system function, the number of immunocompromised patients requiring stronger COVID-19 protection can easily reach tens of millions in the US alone.

Post-Pandemic Considerations

These high-risk patients will continue to need a higher level of personal protection in a post-pandemic period, once the total number of cases subsides. Many experts believe that so-called "herd immunity" is unlikely to be reached in the US any time soon with 30% of the population refusing vaccination and the emergence of new virus variants (Mandavilli, The New York Times, May 3, 2021). The best we can hope for is a lower overall level of the disease continuing to infect new patients but not disrupting everyday life to a point of necessitating lockdowns and other broad isolation measures.

A further consideration for high-risk patients is the regular occurrence of influenza, common cold, and other conventional airborne viruses, along with a risk of emergence of new and yet unknown viruses along with the continued mutations of COVID-19.

The need therefore will continue to exist for high-risk patients to protect themselves from this and other airborne pathogens for years to come, even after the broad mandate for face masks and social distancing is lifted for the general population.

SUMMARY

Accordingly, it is an object of the present invention to overcome these and other drawbacks of the prior art by providing a novel air sterilizer suitable for everyday use that addresses the drawbacks of the prior art.

It is another object of the present invention to provide a novel air sterilizer that can be viewed by a consumer as a fashion item allowing for customization of esthetical styles and individual choice of colors, so as to make it more attractive rather than simply mandatory for the consumers to wear.

It is a further object of the present invention to provide a novel air sterilizer that is comfortable to wear by a non-medical layperson without the need for a tight fit and can be used for extended periods of time.

It is yet a further object of the present invention to provide a novel air sterilizer that can be easily adjusted to vary the level of protection of the user depending on the changing circumstances of the surrounding environment.

The novel air sterilizer features several stages or modes of protection that can be easily switched from one to another. At least some or, in other embodiments, all personal protection hardware elements of the air sterilizer may be mounted on or within a headwear item such as a set of head straps, a hat, or a cap.

A first or minimum stage of protection is an air curtain of disinfected air continuously provided and maintained in front of the user's face. The airflow may be provided by a battery-operated air-handling unit comprising an air pump and a disinfection chamber, for example, a UVC-light chamber. Ambient air may be advanced through the disinfection chamber to inactivate the virus, bacteria, or another airborne pathogen and then directed towards the face of the user. This provides protection when a user is in an area likely containing airborne pathogens. The term "air curtain" is used broadly to include any form of airflow distributed from one or more outlets or nozzles of the disinfection chamber to flow along the face of the user.

A second or intermediate stage of protection is more substantial and includes a face shield that may be positioned in front of the user's face. This provides an additional layer of protection against a stream of potentially contaminated air that may be blown towards the user's face, for example by another person coughing nearby.

An optional third stage of protection is a fabric flap that can be unfolded from the top of the cap to cover the sides and the back of the user's head. Altogether, the positive pressure airflow, the face shield, and the fabric surrounding the user's head may create full protection for the user like that of a PAPR.

BRIEF DESCRIPTION OF THE DRAWINGS

The subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through the use of the accompanying drawings, in which:

DETAILED DESCRIPTION OF PREFERRED EMBODIMENTS OF THE INVENTION

Figure 1A:
FIG. 1A shows a general view of a person wearing a conventional face mask of the prior art.
Figure 1B:
FIG. 1B shows a general view of a person wearing a conventional PAPR of the prior art.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components, and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

While living in a Covid-19-affected area, a person may encounter a variety of situations in which the risk of contracting the virus varies significantly. For example, walking from a personal car to a supermarket involves migrating from a reasonably safe area (one's car) to a less safe but fairly low-risk area (outside parking lot) and then to a higher-risk enclosed space of a supermarket where the person may encounter many other people in close proximity. When in a safe area, a person would not be likely to wear a piece of protective equipment, while entering a higher risk area may justify more inconvenience or efforts in protecting yourself. Wearing an item of "maximum protection" equipment at all times is obviously not practical. Therefore, there is a need for adjusting the extent of pathogen protection allowing to easily increase or decrease the level of protection when moving from one area to the next.

A myriad of everyday situations and environments may be generally classified into four groups:

a. Safe area—may include one's room, apartment, or a house if no one else who is well-known to the user is already sick. This may also include a car used by the same person or shared with a few trusted other users. Being alone outside in the park may also be considered safe. Generally speaking, no protection may need to be used in such a safe area;

b. Minimal risk area—may include walking along an empty hallway or walking into a room where no one else is present. While it is not clear who may have been there a few minutes ago, there are no people within the vicinity of the person—or such people are present, visible, and far enough not to risk a direct exposure. Examples of such an environment may include an empty waiting room in a doctor's office, a barely filled restaurant, taking money out of an ATM, entering a mostly empty office building, etc.

c. Moderate risk area—may include the presence of other people in the vicinity of the user that may or may not obey the rules of social distancing. Examples would include grocery shopping, visiting a bank, visiting with a friend, attending school, working in a cubicle next to others, delivering a package to someone, eating in a restaurant with other people around but not too close, etc.

d. High risk area—may include being unavoidably close to other people, such as riding on a bus or in a subway, flying on an airplane, being in an elevator with other people, etc.

The present invention is conceived to address all of these four areas of risk with a single piece of personal protection equipment (PPE) which is easy to reconfigure in order to adjust to changing surroundings.

Figure 2A:
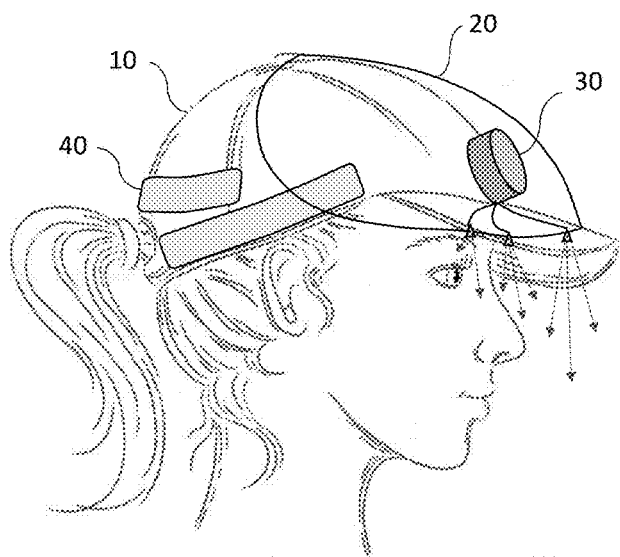
FIG. 2A shows the first stage of protection by a novel air sterilizer with the face shield and the fabric flap up.

At least some or all components of a novel air sterilizer may be mounted on a headband, helmet, or another headwear item. A commonly used baseball cap 10 is used here as an example of such ubiquitous headwear—as seen in FIG. 2A—although the invention is not limited in this regard. In fact, it is envisioned that, at least in some embodiments, the components of the air sterilizer may be provided as a stand-alone kit configured to be mounted on a headwear made in a variety of styles, sizes, and colors. Use of the present invention with a variety of headwear items containing the same air sterilizer components within or on thereof constitutes a key advantage of the invention—by making the air sterilizer esthetically acceptable and more of a fashion item rather than a piece of medical equipment. It is envisioned that a layperson would be more likely to accept, wear, and use the air sterilizer when it looks as much as possible like a commonly available and preferably fashionable item of headwear.

Particular advantages of using a baseball cap 10 for mounting components of the air sterilizer thereon include a universal nature and acceptance of this type of headwear—it is used broadly by men, women, children, the elderly, etc. Typically, such caps are made as one size fits all—with an opening on the back that may be tightened to adjust the cap for various sizes of the head of the user. The present invention may be constructed to avoid positioning components of the air sterilizer in this area of the cap so as to preserve its ability to be size adjusted.

Another advantage of using a baseball cap is the presence of a typically rigid front visor, which may be used for positioning and fixation of the components of the air sterilizer as described in greater detail below.

The novel air sterilizer may feature the following three main components mounted on baseball cap 10: an air-handling unit 30, a face shield 20, and an optional fabric flap 40. Initially, both the face shield 20 and the fabric flap 40 may be configured to be in the "up" or "raised" position—as seen in FIG. 2A.

The air sterilizer of the invention may be placed on the head of the user in a manner very similar to wearing a conventional baseball cap. The air handling unit 30 is off when the user is in a safe area as described above.

The following broadly describes the use of the invention in a variety of circumstances:

First (Minimal) Stage of Protection—FIG. 2A

When entering a minimal risk area, the user may turn on the air handling unit 30, which may be configured to provide a continuous stream of disinfected air coming from one or more nozzles or openings mounted above the face (such as in a visor of the cap). One or more air streams may form an air curtain at least partially surrounding the face of the user, whereby providing a first or minimal stage of protection. In the embodiment shown in the figures, the direction of airflow is from the top towards the bottom. This direction of airflow is advantageous as it urges larger droplets exhaled by the user to land closer to the user and further away from other people. It also urges aerosol formed during exhalation of the user to first travel downwards and be subject to greater dilution as compared to aerosols exhaled by the user in a direction towards other people when not having a face covering. Even when a user is wearing a conventional face mask, the exhaled aerosol is dispersed in all directions depending on the openings and fit of the mask, including sideways and upwards from the user. This increases the chance of infecting a nearby person. The present invention is therefore diminishing that risk by directing both the exhaled droplets and aerosols downwards from under the face shield. Of course, based on local rules and regulations, the user may opt to wear a face mask together with using the air sterilizer of the invention, as using one does not exclude using the other.

In other embodiments, the direction of airflow may be sideways across the face of the user or upwards when the airflow is supplied from below the face of the user as the invention is not limited in this regard.

The ambient air drawn into the air handling unit may be disinfected inside thereof as described below in greater detail and then supplied to the user for safe breathing with reduced or even no risk of inhaling the virus from the ambient air. The air handling unit may be sized to provide a sufficient volume of air to the user to be close to or exceeding a natural volume of inhaled and exhaled air, typically at least 5-10 liters per minute. A child version of the invention may be scaled down to support the suitable breathing needs of that user, typically at or above about 3 l/min. In embodiments, the air handling unit may be configured to process air flows of at least 3 l/min, at least 4 l/min, at least 5 l/min, at least 6 l/min, at least 7 l/min, at least 8 l/min, at least 9 l/min, at least 10 l/min, at least 15 l/min, at least 20 l/min, at least 30 l/min, or at least 40 l/min as the invention is made suitable for a variety of circumstances.

Providing only an air curtain or otherwise distributing the flow of disinfected air adjacent to the face of the user as a minimal means of protection has many advantages when the user is present in a minimal risk area—there is nothing present physically on the face, the user can easily breathe, speak, eat and drink. The face of the user is also fully visible to others or video communication equipment nearby making any non-verbal interaction more natural.

Figure 2B:
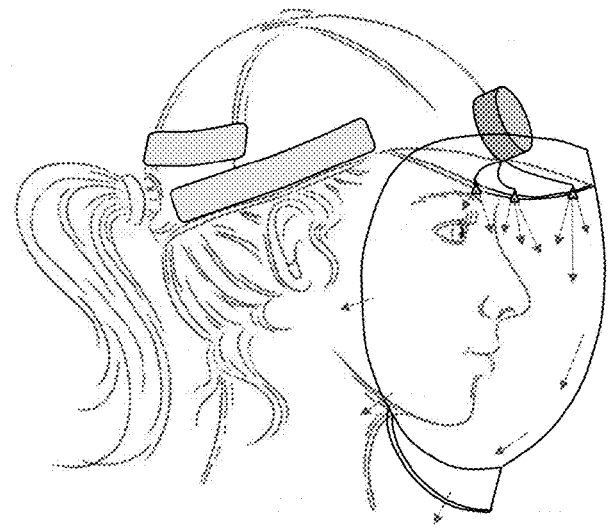
FIG. 2B is an illustration of the same switched to an intermediate stage of protection—with the face shield down but the fabric flap still up.

Second (Intermediate) Stage of Protection—FIG. 2B

The air curtain may not provide adequate protection when entering a moderate risk area. Direct sneezing or coughing by another person or a gust of wind towards the user may cause the virus droplets to penetrate the air curtain and increase the risk of exposure. To reduce or even avoid that risk, the user may move the face shield 20 from the "up" position to the "down" position—as seen in FIG. 2B. Importantly, the clean air from the air handling unit 30 may still be directed inside the space between the face shield 20 and the face of the user so as to provide both the air curtain protective effect and the face shield protection action.

Advantageously, the face shield may be moved down partially—so as to adjust its position depending on the situation. A partial lowering of the face shield may be useful when eating in a restaurant, for example. In this case, the upper area of the face may be protected by the shield while the lower area is still open adjacent to the mouth of the user to facilitate food intake. Continued air curtain or disinfected airflow would still be present in that case.

When leaving the moderate risk area and entering the minimal risk area, the air sterilizer may be adjusted again to move the face shield up so as to leave only the air curtain blowing as a single layer of personal protection.

A further advantage of a face shield in addition to the air curtain of disinfected air is the protection of the eyes and other parts of the face that are typically left bare when using a conventional face mask.

Figure 2C:
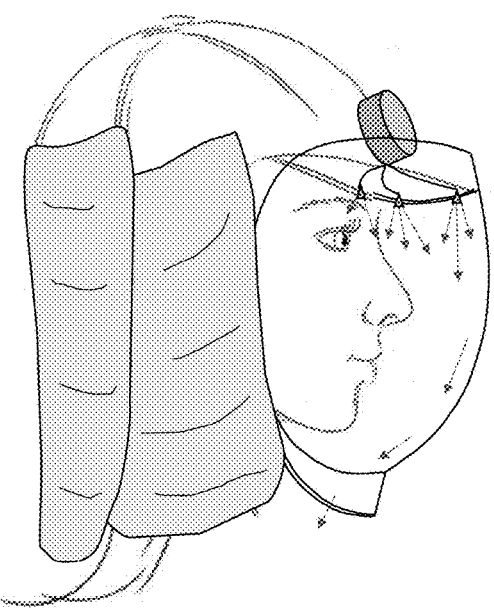
FIG. 2C shows the same device when configured for maximum protection with both the face shield down and the fabric flap unfolded to cover the entire head of the user.
Figure 3:
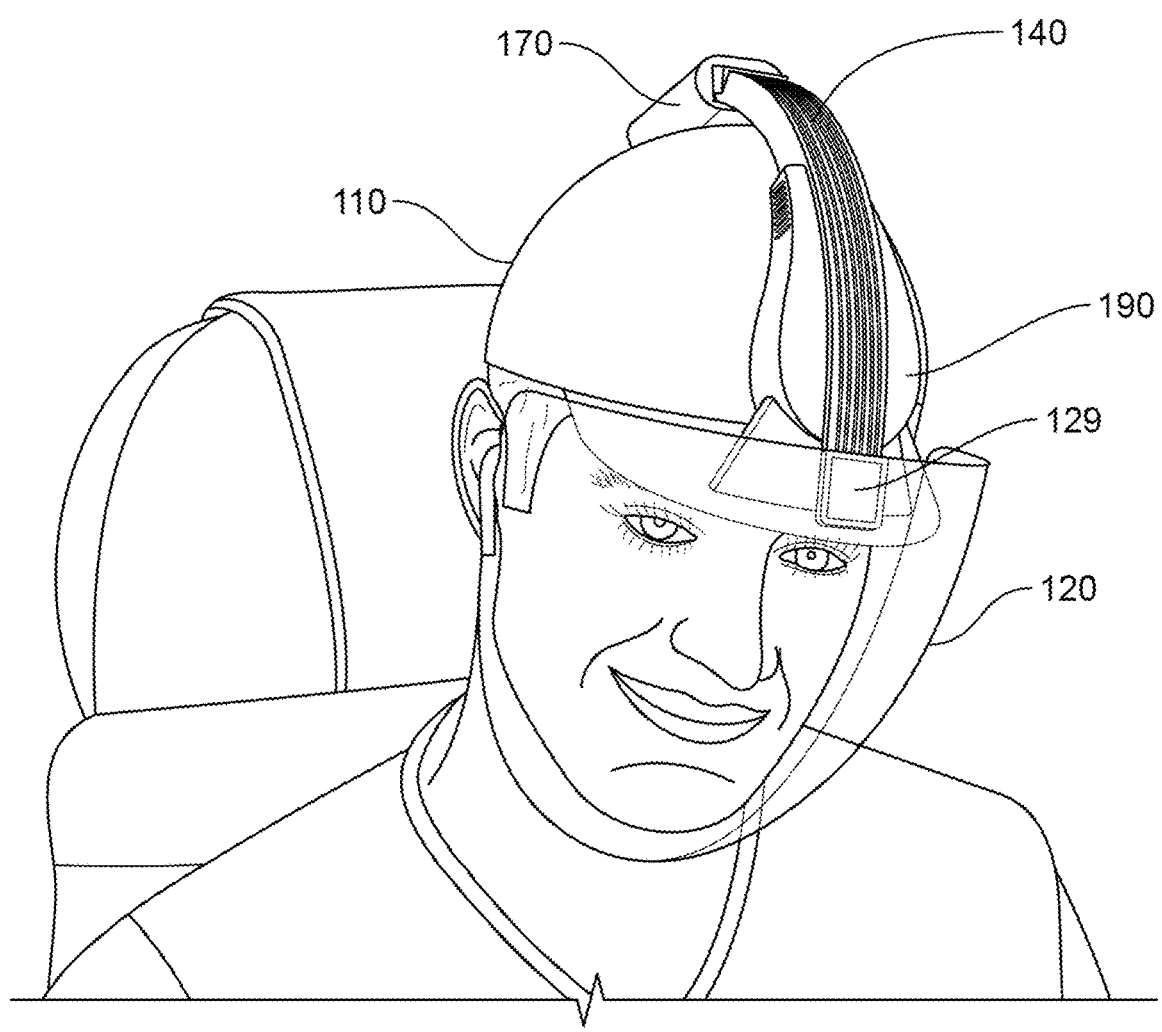
FIG. 3 shows a perspective view of one exemplary design in use.
Figure 4:
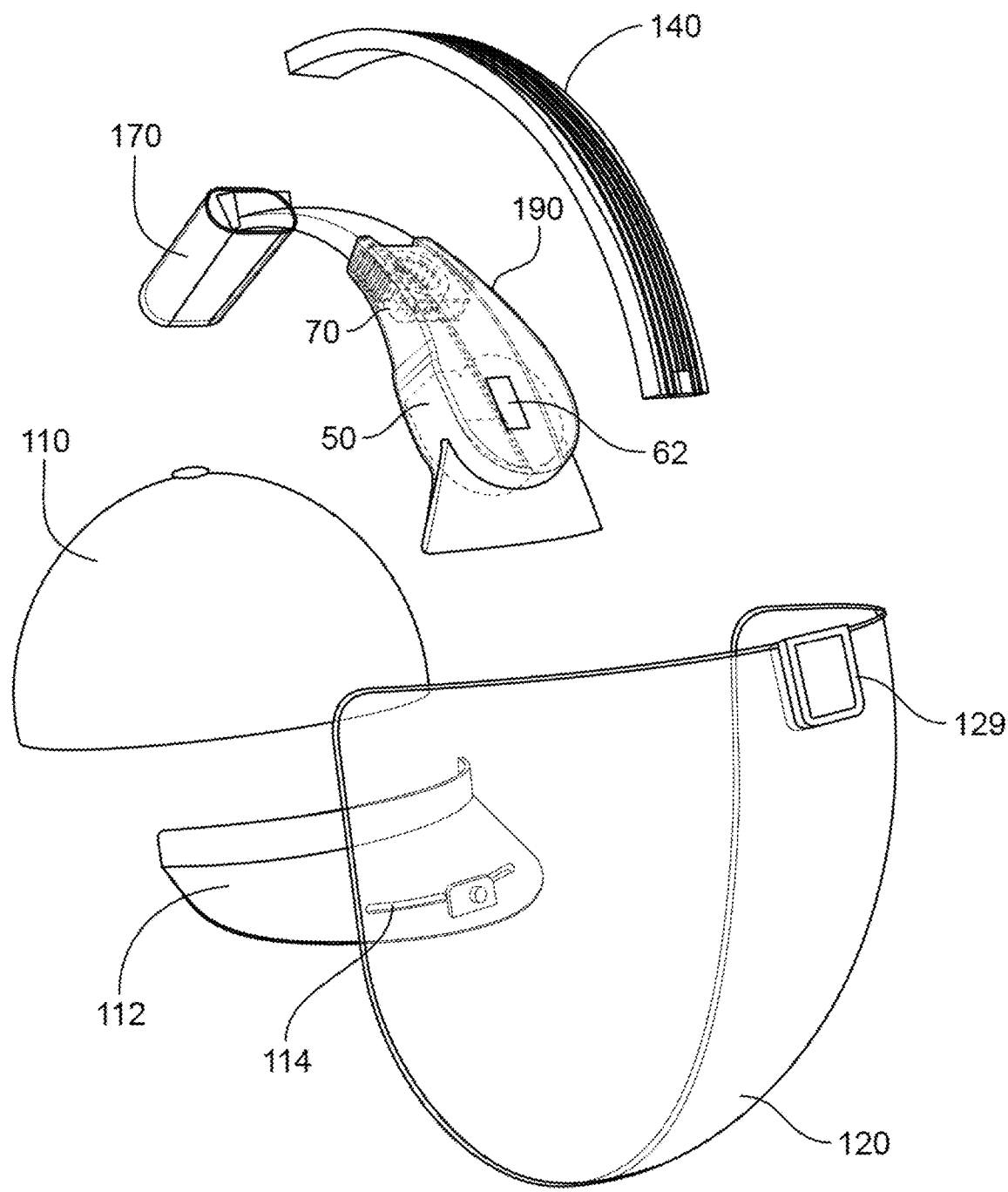
FIG. 4 is an exploded perspective view of the main components of the device.
Figure 5:
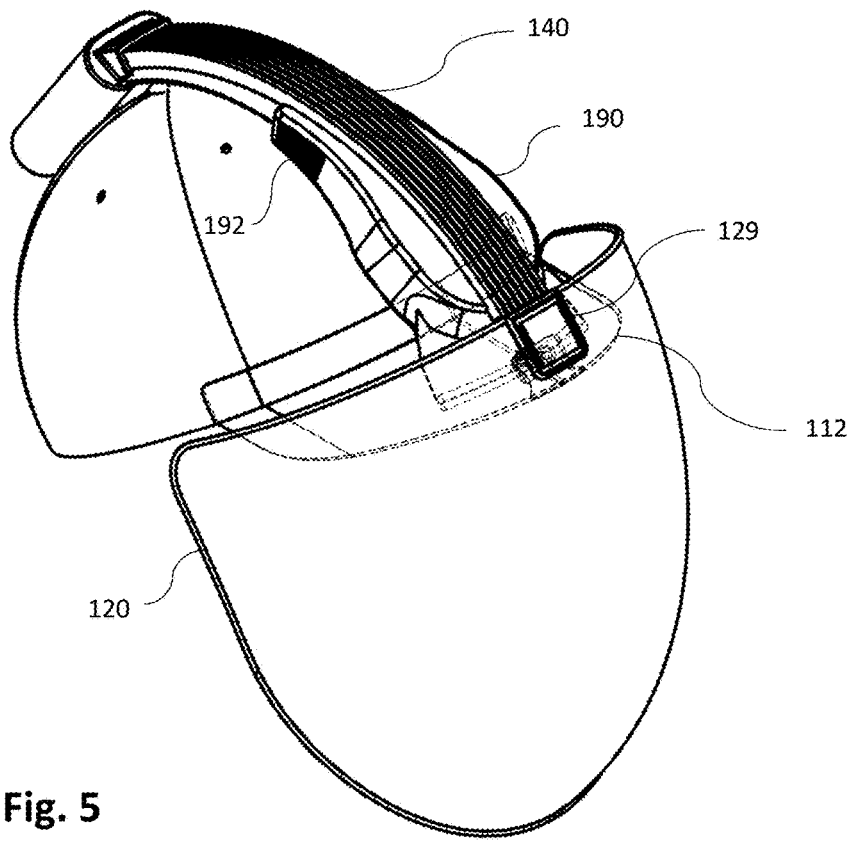
FIG. 5 is a perspective view of key components of the device of FIG. 4.

Third (Maximum) Stage of Protection—FIG. 2C

When entering a high-risk area for virus contamination with many people surrounding the user in close proximity, the user may further increase the extent of personal protection by unfolding an optional fabric flap 40 as seen in FIG.

2C. The fabric flap may contain one or more panels, as seen in FIG. 2C. The air sterilizer of the invention at this point converts to a configuration similar to a full PAPR when the entire head is covered and isolated from the ambient environment with positive pressure ventilation provided by the air handling unit 30.

Importantly, different parts of the air sterilizer do not need to form an airtight seal between themselves. It may be sufficient for these components to overlay each other as small openings would not present an increased risk of contamination due to airflow from within the air sterilizer area towards the outside thereof.

Once the user leaves the high-risk area, the fabric flap may be lifted and folded up to convert the air sterilizer to a lower level of protection. In other circumstances, for example, at the end of the day, the cap may be inverted to expose the inner portion of the cap material and fabric flap components. The fabric of the flap and/or the back portion of the cap may be brought over the front portion of the cap so as to enclose the presumably contaminated external surface area of the air sterilizer within thereof. The fabric may be configured to form a bag that may be closed, for example by pulling a drawstring or using one or more snaps—so as to isolate all of the contaminated surfaces of the air sterilizer inside thereof. The item can then be transported safely to a cleaning area, for example at the home of the user.

To disinfect the air sterilizer, the user can detach a face shield and remove the air handling unit from a flap or a fabric pocket that may be formed on top of the cap visor. These two components may be wiped with a disinfecting solution and the rest of the cap may be sanitized, for example by machine washing. Reassembly of the air sterilizer after recharging the batteries of the air handling unit may prepare it for another use.

One exemplary embodiment of the invention is shown in FIGS. 3-13 and may include:
- a headwear such as a baseball cap 110 made from a flexible fabric with a rigid visor 112,
- a housing 190 containing an aft pump 70 and a disinfection chamber 50 inside thereof and configured to draw the ambient air in through a suitable opening or a series of openings 192 and supply sterile air in one or multiple streams through an outlet 194 forming an aft curtain directed from the slot 114 of the visor 112 and downwards toward the face of the user,
- an arch-shaped guide rail 140 extending from the lower part of the housing 190 near a visor 112 towards the top of the cap 110 along a circular trajectory, which may have a number of extruded fins to achieve the desired heat distribution as discussed below in greater detail,
- a face shield 120, which may be curved along its central line to match the circular arch curvature of the guide rail 140. The face shield 120 may be slidingly attached to the guide rail 140 by the engaging button 129, which in turn may be configured to at least partially envelope the guide rail 140 and retain the face shield 120 at one, two, three, four, five positions, or any desired position along the guide rail 140, such as exemplary positions 120a, 120b, and 120c, and
- a battery housing 170 with one or more rechargeable batteries located inside thereof, which may be positioned at the top of the cap 110 or towards the back thereof to achieve a balanced weight distribution of the device around the head of the user.

The size of the headwear item 110 may follow conventional "one-size-fits-all" baseball caps that have an adjustment capability in the back to increase or decrease their circumference. It is anticipated that the device will be universally applicable to most adults if that convention is followed, A separate scaled-down version may be created for children. The fabric portion of the device may be detached from the housing 190 such that it can be washed or replaced if necessary. The fabric portion may be detachably assembled with the visor 112 and/or the housing 190 using snaps, Velcro, or other similar temporary fastening means, as the invention is not limited in this regard. The visor 112 may be either securely attached to cap 110 and detachably attached to the housing 190 and the rest of the device, or it can be a permanent part of the housing and detachably attached to cap 110. In further embodiments, the cap 110 may be disposable and replaced between different users of the device.

A slidable and optionally removable face shield 120 may be designed to allow rapid adjustment of its position. The face shield 120 may be made from a rigid or flexible polymer. In embodiments, the face shield 20 may be entirely clear or tinted to a desired degree so as to avow the use of the air sterilizer outside in sunny conditions. In further embodiments, the face shield 120 may be covered with a coating on its outer surface. Such coating may be configured to change the extent of transparency such as make the face shield more tinted outdoors and less tinted indoors.

In further yet embodiments, the outer coating of the face shield may have anti-microbial properties to facilitate a self-disinfection of the face shield 120 over time, for example overnight. Examples of such transparent coatings include coating containing small particles of copper, silver, zinc, and other metals as well as their respective salts. In one example, copper nanoparticles may be incorporated in a coating of the face shield 20 comprising about 01.-1% of copper by weight. This design may not appreciably limit the transparency of the face shield 120, while at the same time it may allow for the inactivation of pathogens on its surfaces within a few hours of exposure. Storing such a face shield overnight would effectively self-disinfect the surface thereof and prepare it for another use.

Figure 7:
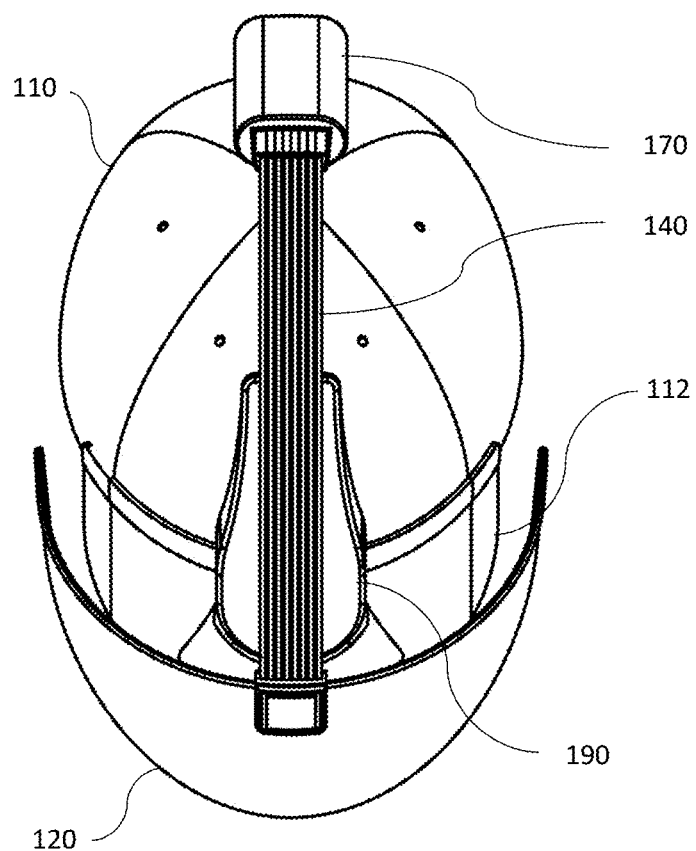
FIG. 7 is a top view of the same.
Figure 8:
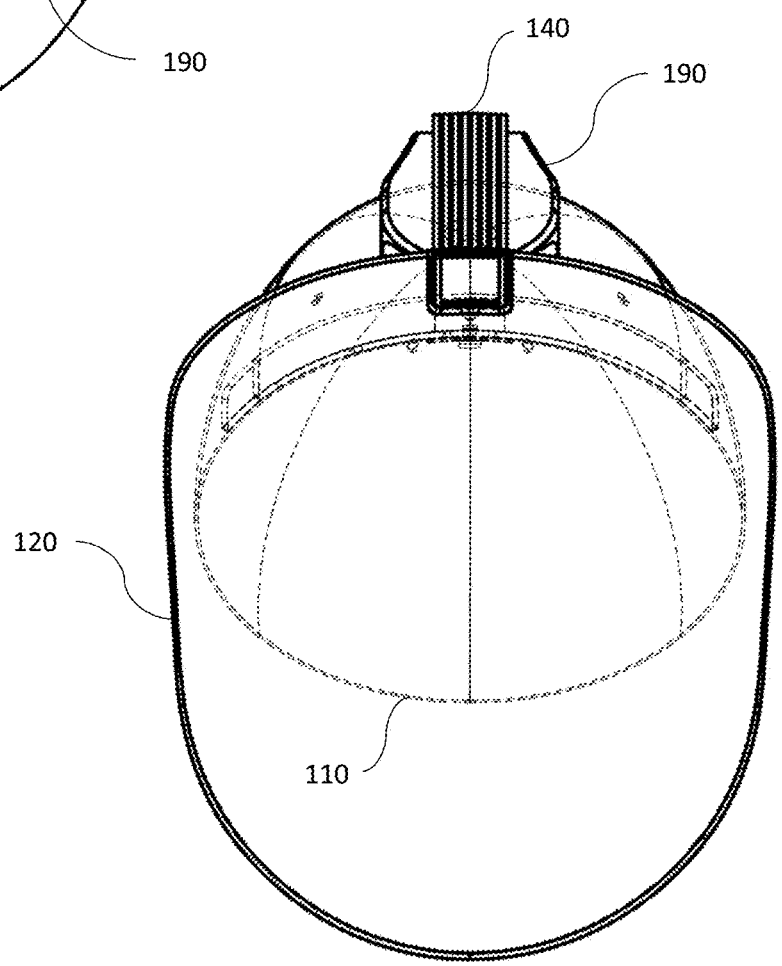
FIG. 8 is a bottom perspective view of the same.
Figure 10:
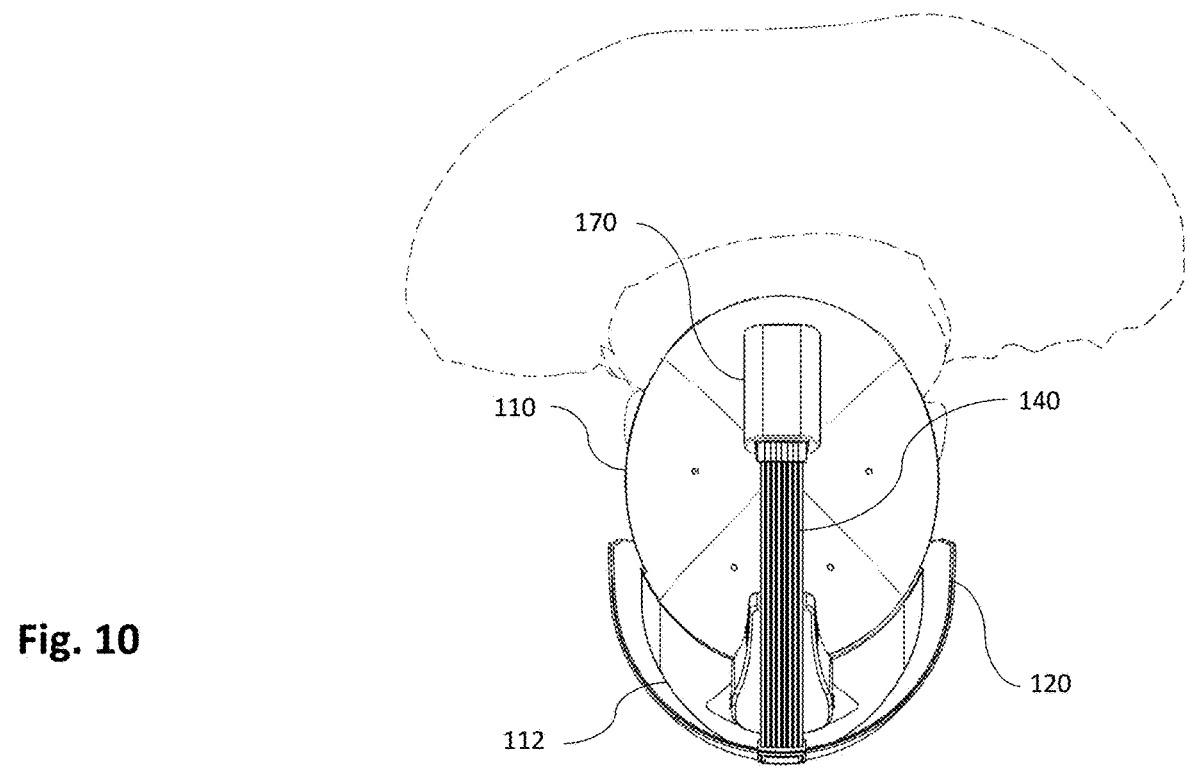
FIG. 10 shows a top view of the same as in FIG. 9.
Figure 11:
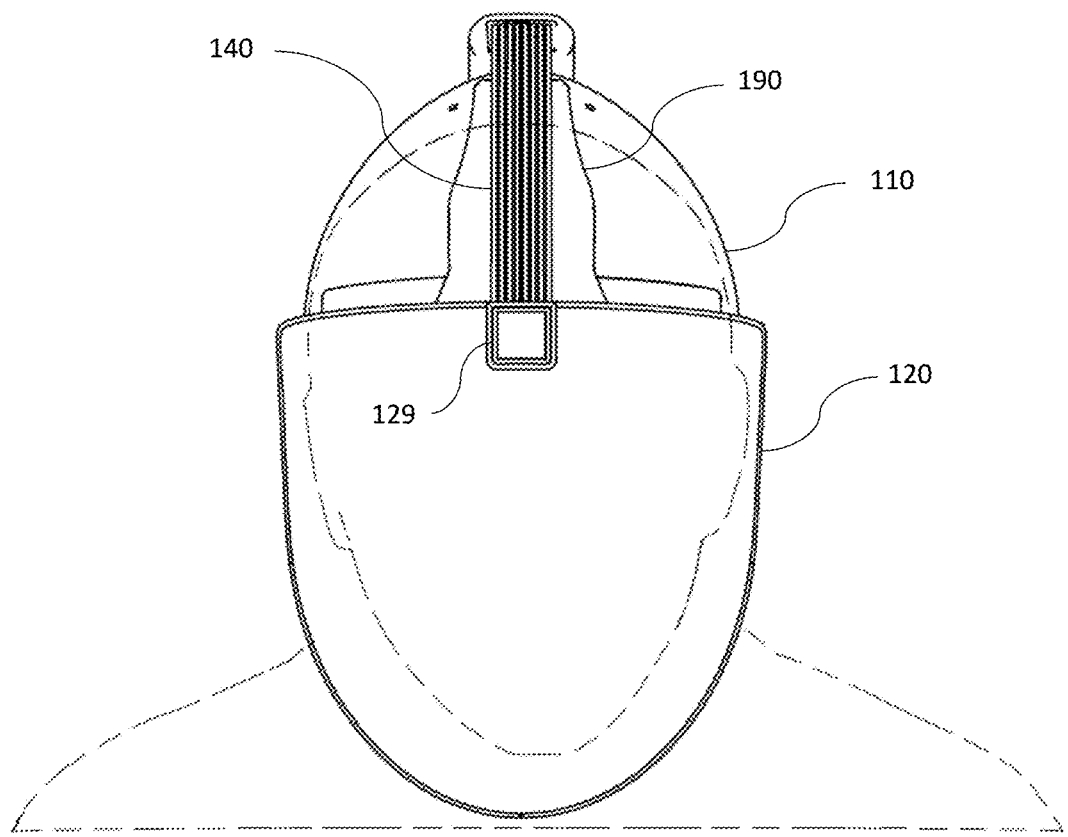
FIG. 11 is a front view of the same as in FIG. 9.

A visor 112 of the cap 110 may extend from the cap by about 3 to 5 inches. At the same time, the face shield 120 may be positioned about 1-2 inches away from the face so as to account for glasses, beard, and other items protruding from the face of the user—as best seen in FIGS. 7 and 10. Placing the face shield 120 closer to the face of the user may make it uncomfortable while extending it further away may cause an unnecessary increase in its size.

An engaging sliding button 129 may be formed in the middle of the upper edge of the face shield 120 and configured to be the sole attachment point between the face shield 120 and the guide rail 140, The cross-sectional shape of the guide rail 140 may be in a form of a trapezoid such that a portion of the engaging button 129 may "hug" the external fins of the guide rail 140 to slide thereon. The engaging button may be equipped with a spring-activated brake positioned to secure the face shield 120 in its current position on the guide rail 140. Depressing the top of the engaging button 129 causes a release of the brake and frees up the face shield 120 to move up and down the guide rail 140. Release of the button would cause the face shield 120 to be retained at a desired position along the guide rail 140.

When the face shield 120 is moved to its maximum "up" position 120a, the lower edge thereof may be made to coincide with the outer edge of the visor 112. At the same time, moving the face shield 120 to its maximum "down"

position 120c would bring the engaging button 129 to the lowest part of the guide rail 140, typically on top of the visor 112.

Figure 6:
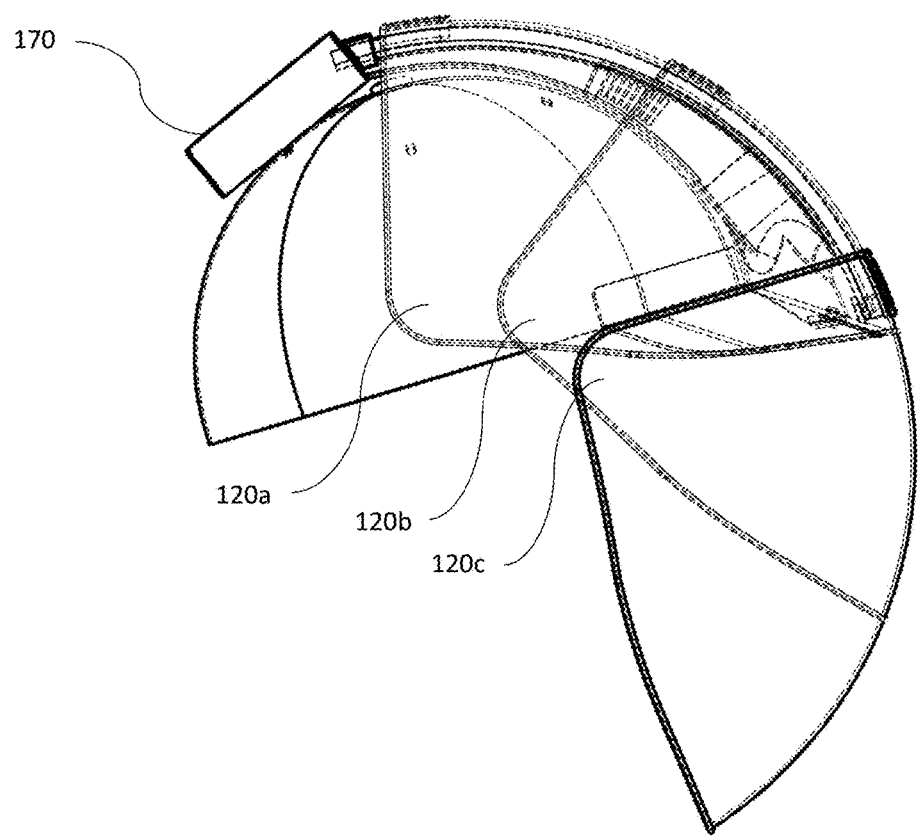
FIG. 6 is a side view of the same with three positions of the face shield outlined.
Figure 9:
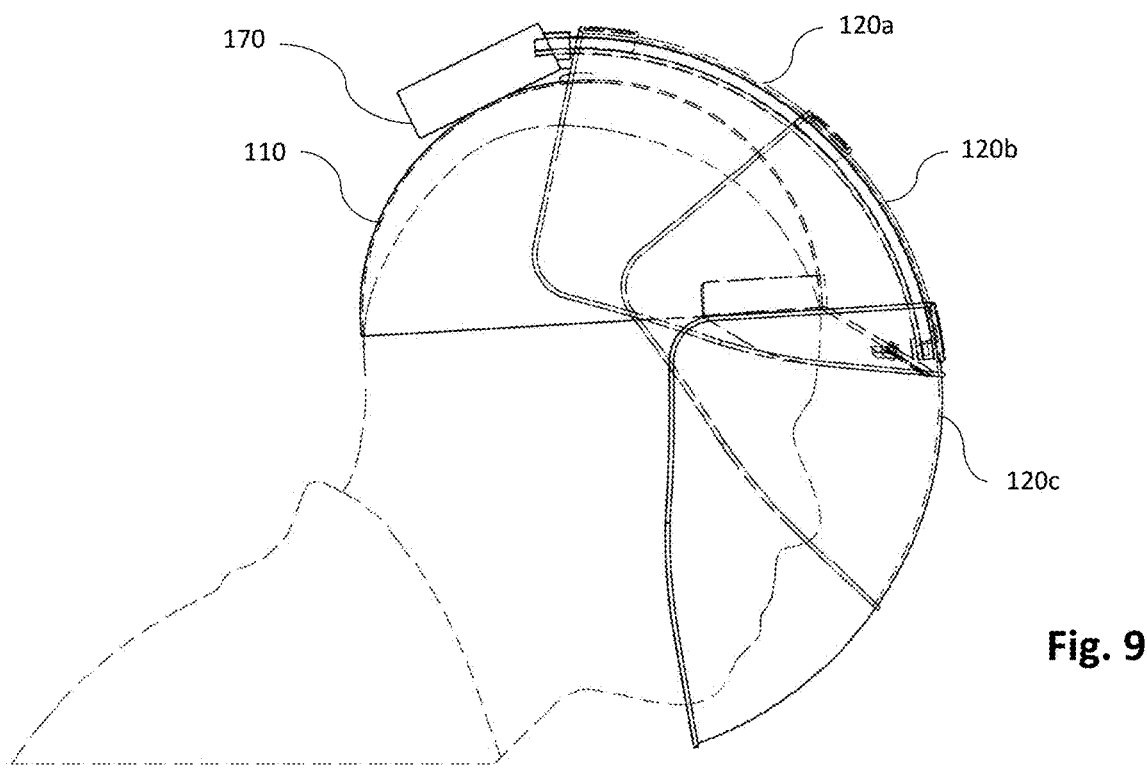
FIG. 9 is a side view of the same shown in use on a subject.

The curvature of the guide rail 140 may be made to be concentric with the curvature of the face shield 120. In this case, raising the face shield 120 would cause it to be positioned next to the guide rail 140 as best seen in FIGS. 6 and 9.

The guide rail 140 may be attached to the arch-shaped top of the housing 190 along the grooves 196 and may be made from Aluminum or another heat-conducting material. A series of parallel fins or other heat-dissipating geometry may be implemented for the guide rail 140 to facilitate its dual use as a heat sink for the UVC LEDs as explained below. The number of fins may range between 2 and 30. The thickness of the fins may range from about 0.5 mm to about 4 mm. The guide rail 140 in this case may be placed in close heat-transferring contact with one or more LEDs and used both as a heat sink as well as a guide for the face shield 120 sliding over its outer surface.

The housing 190 may be made to contain the air disinfection chamber 50, the air pump 70, support the guide rail 140 and the battery compartment 170, as well as house the controller board and internal wiring of the device. The housing may be made from the lightweight opaque polymer by injection molding or another suitable manufacturing process.

Air Disinfection Chamber

Figure 12:
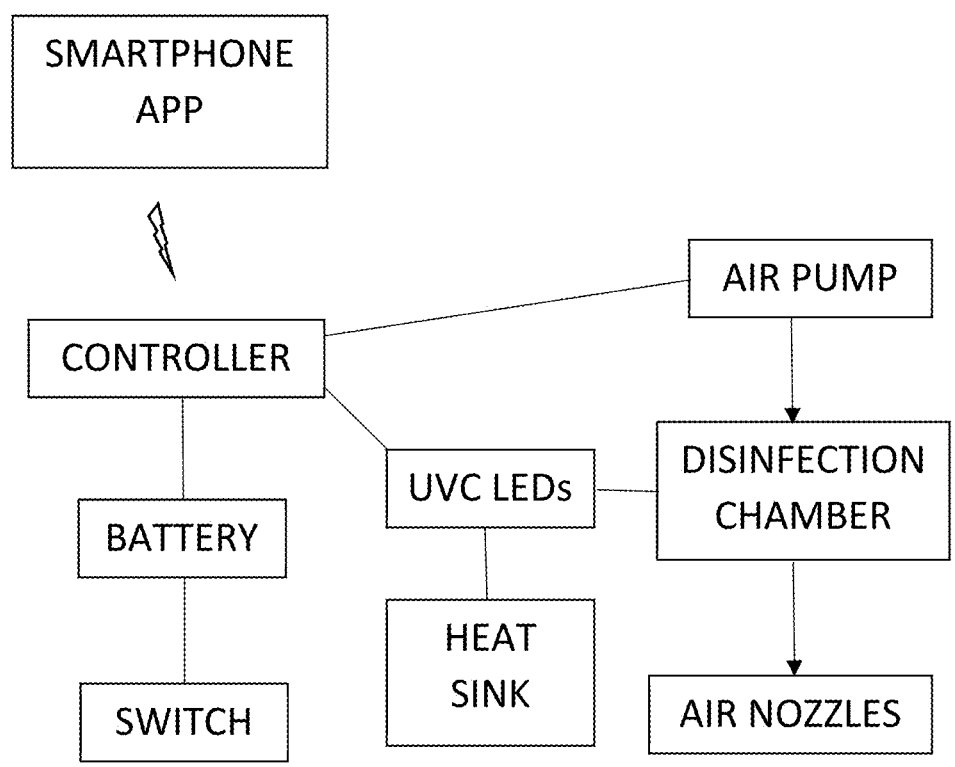
FIG. 12 shows a block diagram of one example of the air sterilizer of the present invention.
Figure 13:
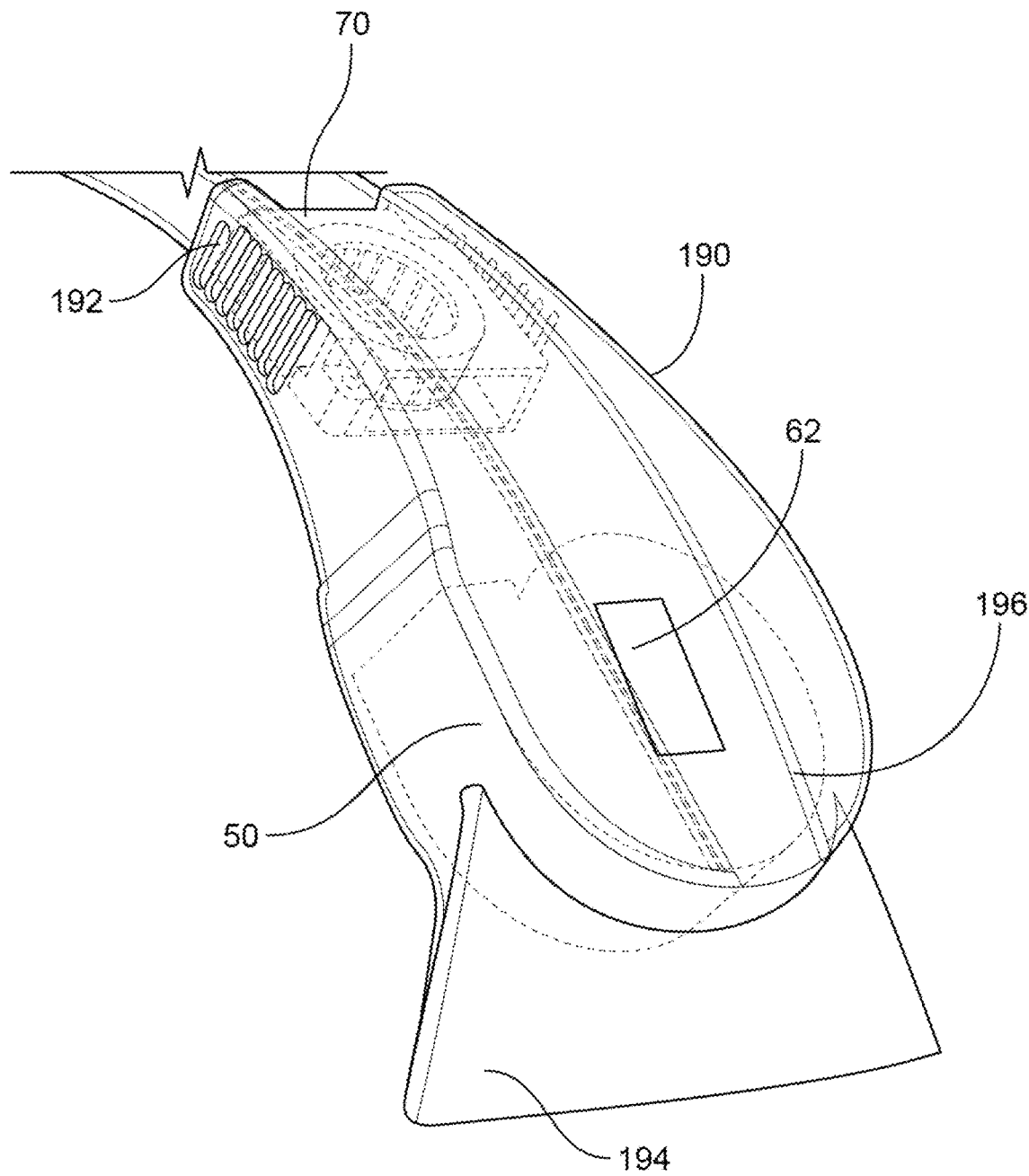
FIG. 13 is a close-up perspective view of the housing containing the disinfection chamber and the air pump.

A general schematic diagram of the air handling assembly including the air disinfection chamber 50 is seen in FIG. 12 and closely illustrated in FIG. 13 with the housing 190 shown as a semi-translucent component for better clarity. The assembly may include a rechargeable or a single-use battery pack 170 proving electrical power thereto. One or more rechargeable and optionally replaceable batteries may be provided to energize the air handling assembly making the device portable and wearable by the user. The capacity of the battery pack 170 must be considered carefully with a view of achieving a balanced combination of operating time and the weight and size of the device as a longer operating time may conflict with usability factors. To reduce the size of the battery, a plug-in cable may be provided to supplement the onboard power with an external power source, such as for example a power bank used for common smartphones or a plug-in arrangement to use wall power. Plugging in the device may be used for both energizing the air handling unit as well as for recharging the batteries. Limited mobility of the user in case of using a cable may still be acceptable in a variety of situations, such as charging the battery while flying on an airplane or working at the same place for extended periods of time. Examples of workers staying at the same place most of the time include a cashier in a store, a worker at a meat plant, a schoolteacher, etc.

Lithium ion, lithium polymer, or other suitable rechargeable batteries may be used for the purposes of the present invention. One or more batteries may be positioned next to the air handling assembly or placed in other locations on the cap, which may allow for better weight distribution and balance around the head of the user.

The air sterilizer may be equipped with an external visible LED light, for example, blue light LED, which may be activated upon turning the device on. This will indicate to the user and observers that the device is operating. Changing the color of the LED to yellow may be used to indicate low battery status. Turning the LED in red color may be used to indicate a malfunction or a need for repair.

The air handling assembly may further include an air pump 70 operated by a controller. The air pump 70 may be selected, for example, from a line of laptop or desktop computer fans or other small air turbines. An air pump with low noise and vibration may be preferred, such as for example by those equipped with a brushless DC motor. The airflow capacity of the air pump may be selected to satisfy the average volume of air typically inhaled by an adult subject, from about 5 liters per minute to about 10 liters per minute. A higher capacity may be selected to assure a certain safety factor for the user or to provide protection in situations of increased air volume consumption, such as during exercise. A higher capacity requirement for the air pump has to be balanced against a desired minimal weight and noise as larger capacity air pumps tend to be also physically larger and consume more electrical power during their operation.

In alternative embodiments, more than one air pump may be used and mounted in various places around the cap of its visor. In this case, each air pump may be made smaller than a single air pump 70 as described above. One example of an air pump that may be utilized in such an arrangement is a disk pump produced by TTP Ventus (Melbourne, UK). These pumps can currently produce up to 2 l/min of airflow while being silent, having low weight, and very small size—at about two quarter coins each. In embodiments, 3 or 4 such pumps may be mounted directly over the visor of the cap at the nozzles of the air sterilizer or in other convenient locations.

The air pump 70 may be configured to advance the ambient air through an air disinfection chamber 50, which may be located upstream of the pump 70, within the housing 190, or downstream from the air pump 70 as the invention is not limited in this regard. The air disinfection chamber 50 may include a filter such as a HEPA filter in some embodiments, while in other embodiments it may be designed to avoid using any filtering elements. Such a "filtration-free" design may be advantageous to that featuring a filter because moving air across a filter may cause significant resistance to airflow and a subsequent pressure drop, which may necessitate selecting a more powerful air pump. This may lead to increased weight and reduced operation time of the air sterilizer. Pushing air through a low resistance open-air path disinfection chamber may be, therefore, preferred as it may be done with a smaller and lighter air pump.

As opposed to a conventional PAPR device designed to remove a variety of contaminants from the air, the present air sterilizer may be designed to only handle a threat from an airborne pathogen, such as bacteria or viruses. It may be assumed that other than a risk of pathogen contamination, the ambient air is OK to breathe. Such a design may use an air disinfection method based on UV irradiation, which does not involve air filtration and therefore may be done using a smaller air pump 70.

Ultraviolet Germicidal Irradiation (UVGI) is a disinfection method commonly used in hospitals and medical settings to destroy airborne microorganisms and pathogens. UVGI is most often utilized as a UV lamp in the operating room for air purification or a lighted box for toothbrush disinfection. This method of disinfection is increasing in popularity due to its efficacy and ease of use. Ultraviolet Germicidal Irradiation has been used in many surface and air disinfection applications since the mid-20th century. More recently, it has been used for medical and hospital applications such as air sanitization as well as disinfection of equipment, instruments, and operating rooms, as well as in consumer applications such as disinfection of a cellphone or a toothbrush.

UVGI works by affecting the DNA of bacteria or viruses. A short ultraviolet wavelength is used to disrupt the DNA of the pathogen by destroying the nucleic acids and removing its reproductive capability. The germicidal range of ultraviolet radiation is classified as "UV-C" and is within a range of about 100 to about 290 nm wavelengths—the peak of this wavelength may be in a range from 250 nm to 270 nm and more specifically about 265 nm. If the ultraviolet radiation is within this range or reaching the peak, it is then able to disrupt the DNA and therefore able to remove the reproductive capability of bacteria and disable the virus. UV-C radiation range is the most germicidal, followed by UV-B and UV-A ranges of ultraviolet wavelengths.

For embodiments of the present invention, a small air disinfection chamber 50 may be placed within the air handling unit of the housing 190. The source of UVC irradiation may be one or several UVC lamps or light-emitting diodes (LEDs) 62, 63 (see FIG. 15), for example, Klaran LEDs produced by Crystal IS Inc. (Green Island, NY) or LEDs produced by Luminus Devices Inc (Sunnyvale, CA). Each LED is only a few millimeters wide in size so several of these LEDs may be mounted at the center or be spread throughout the disinfection chamber 50. Each LED may emit anywhere between 4 and 100 mW of optical power output at the peak wavelength in the UVC range, so only 1, 2, or 3 of the higher output LEDs may be needed to achieve the desired irradiation dose (two LEDs 62 and 63 are shown in the drawings as a non-limiting example). LEDs with a wide viewing angle of about 110-150 degrees may be used so as to maximize the width of the effective area of irradiation coverage. Optical lenses may be placed in front of the UVC light source so as to optimize irradiation distribution for a given geometry of the disinfection chamber 50.

LED life and extent of output degradation may be monitored by the electronics of the controller. Once LED output is below a predetermined useful threshold, the controller may be configured to signal to the user to replace the LED of the entire device by either (i) not turning on the fan at the start of the operation, or (ii) turning on the fan in an alternating checkered pattern—5 sec on, 5 sec off, to indicate that something is wrong and needs attention.

The air disinfection chamber 50 may be designed to contain all UVC irradiation inside so as to avoid exposure of the subject to the UV light outside the device. The disinfection chamber 50 may be made from suitable materials selected to avoid damage from UVC irradiation, for example by using metal or metalized internal surfaces.

The UVC light source 62 may be positioned at the top of the disinfection chamber 50 to shine downwards at the entire volume thereof. To further increase the extent of air disinfection, the air disinfection chamber 50 in other embodiments may be made to direct airflow in circles or spirals around thereof or to form one or more flow stagnation zones or vortexes, whereby increasing the resident time of air articles inside the chamber for a longer exposure to the UVC light.

Figure 14:
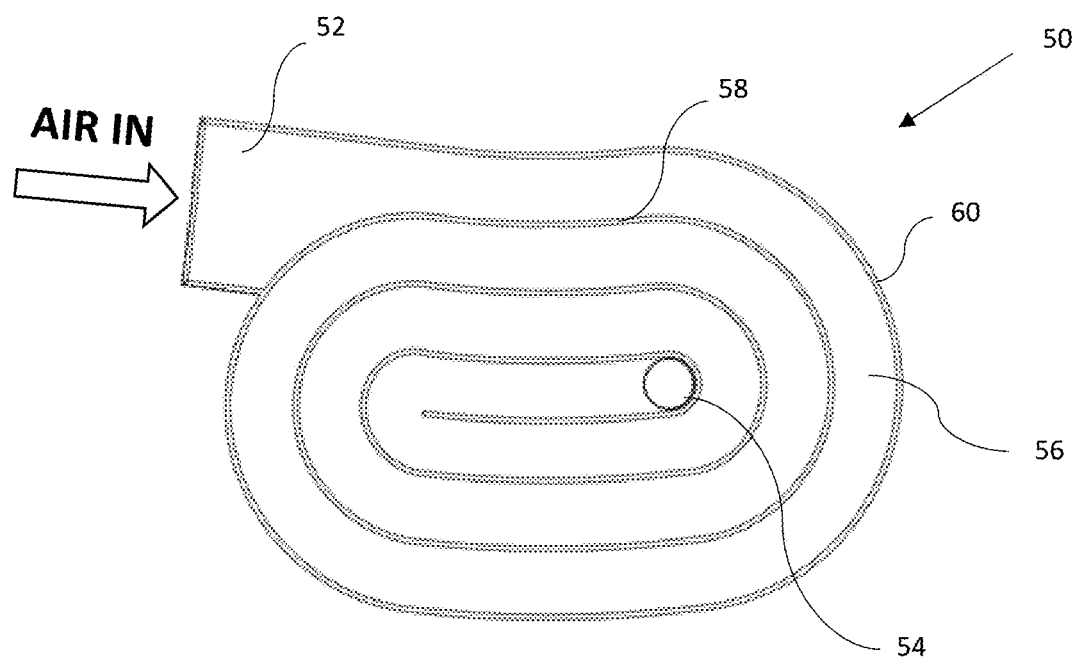
FIG. 14 shows a cross-sectional view of the disinfection chamber of the device.
Figure 15:
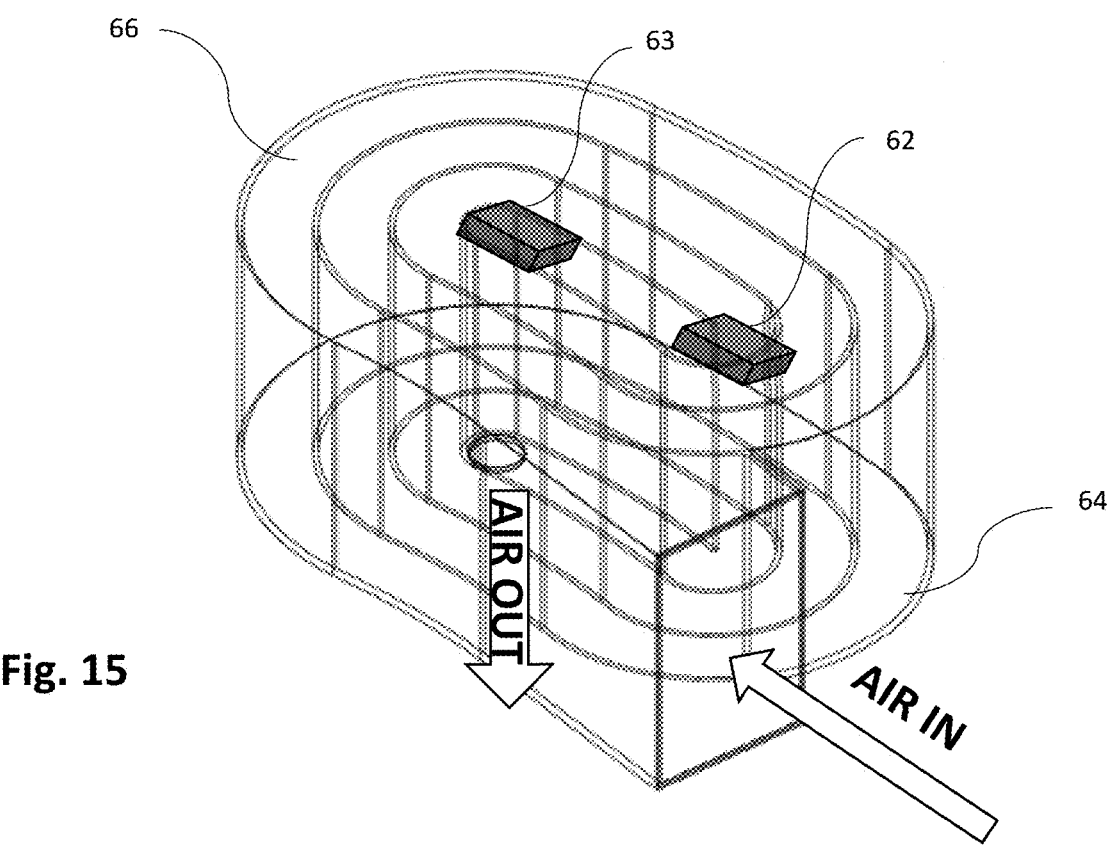
FIG. 15 shows a perspective view of the same as in FIG. 12.

A further design of the disinfection chamber 50 is now described in more detail as shown in an example in FIGS. 14-15. The main objective of the air disinfection chamber 50 is to expose the airflow to the UVC irradiation inside thereof at a sufficient dose to inactivate the airborne pathogen. In the case of Covid-19, studies show that a UV exposure dose of about 3 to 5 $mJ/cm^2$ may be sufficient to achieve 2 log inactivation or more of the virus. That means that at least 99% or greater of the virus is destroyed as a result of UVC exposure inside the disinfection chamber 50. A lower dose of at least 1 $mJ/cm^2$ may still be sufficient to achieve at least 90% viral load reduction, which may still be acceptable as a better alternative to face masks. Achieving this inactivation exposure while providing the disinfection chamber to be sufficiently small in size and weight to be wearable on the head of the user is not a trivial task. A further design challenge is to assure proper heat dissipation from the LEDs to maintain them at a suitable operating temperature. UVC LEDs are very small in size but not efficient in converting electrical energy to UVC irradiation and are known to generate a significant amount of heat. Rising temperature is known to degrade LED performance and therefore may jeopardize the efficacy of air disinfection. For this reason, it is advantageous to provide a large heat sink capable of passively dissipating the heat generated by the LEDs during operation.

An exemplary air disinfection chamber 50 (FIG. 14 and FIG. 15) may be designed to provide about 2 log virus reduction for an airflow of about 15 linin, which may be sufficient to satisfy normal at-rest breathing for an adult subject, even accounting for dissipation of sterile air after mixing with ambient air in the vicinity of the air curtain. The disinfection chamber 50 may include at least one inlet 52 for air to enter the disinfection chamber from the outlet of the air pump 70. If more than one air pump is used to move the air through the device of the present invention, additional inlets may be located throughout the air disinfection chamber 50. The size and volume of the disinfection chamber 50 may be selected to maximize residence the time of air particles inside thereof while at the same time minimizing the overall bulk and weight of this component.

While in some embodiments the internal space of the disinfection chamber 50 may be empty and configured to provide for one or more natural vortex formation in order to extend air particles residence time, in other embodiments the airflow path may be delineated using one or more internal walls 58. FIG. 14 shows a generally spiral arrangement of the airflow pathway 56 from the entrance 52, around the peripheral wall 60 of the disinfection chamber 50, along internal walls 58, and gradually extending towards its central area leading to an exit 54. Serpentine, zigzag, multilevel, back-and-forth, and other types of flow pathways may also be used as the invention is not limited in this regard. importantly, the entire pathway of the airflow is collected together in a generally circular or oval boundary and exposed to the UV light to as to maximize the UV disinfection effect on the passing airflow.

In embodiments, a width of the airflow path 56 may be selected to be from about 4 mm to about 12 mm, such as 4, 5, 6, 7, 8, 9, 10, 11, or 12 mm as the invention is not limited in this regard. The height of the air chamber and therefore of each segment of the airflow may be selected to be about 10-30 mm, such as 10, 15, 20, 25, 30, or any dimension in-between, as the invention is not limited in this regard. the diameter of the air disinfection chamber, in this case, may be from about 30 mm to about 80 mm, such as at least 30 mm, at least 40 mm, at least 50 mm, at least 60 mm, at least 70 mm, or about 80 mm. The airflow pathway in this case is elongated and arranged to be exposed to the ultraviolet irradiation emanated from the LEDs 62 and 63. The length of the airflow pathway may be anywhere from about 50 mm to about 400 mm, such as at least 50 mm, at least 75 mm, at least 100 mm, at least 150 mm, at least 200 mm, at least 250 mm, at least 300 mm, at least 350 mm or at least 400 mm.

An optimization calculation may be performed to vary both the width and the height of the airflow path 56 and its overall cross-sectional profile in order to assure an even distribution of airflow within each segment of the spiral pathway while maximizing the residence time and minimizing total airflow resistance inside the disinfection chamber 50.

The disinfection chamber 50 may include a top cover 66 containing the LEDs and the bottom cover 64. To maximize the use of the UVC irradiation from the LEDs, the internal surface of the top cover 66, bottom cover 64, and sidewalls. All or at least some of these surfaces may be coated with or made from a UV-reflective material, such as ePTFE (Polytetrafluoroethylene), other fluoropolymers, or aluminum. This will provide for reflection of UVC rays and increase the exposure of the airflow to UVC irradiation.

Covering at least one internal surface of a bottom 64, one or more sides 60, or a top 66 of the air disinfection chamber 50 with an "optical PTFE" film may be especially advantageous to disperse UVC irradiation more evenly within the disinfection chamber 50. One example of such optical PTFE film is a Spectralex Optical Diffuser Film manufactured by Lake Photonics GmbH (Germany).

Internal wall 58 may be made from a UV-transparent material, such as FEP (Fluorinated ethylene propylene) film commonly used in 3D printers in order to not create shadows inside the disinfection chamber and to avoid shielding of airflow from UVC irradiation.

One or more heat sinks may be provided to dissipate the heat generated as a result of operating UVC LEDs. In embodiments, each individual LED may be provided with a dedicated heat sink. In other embodiments, groups of LEDs or the entire LED assembly may be provided with a single heat sink. In one example, the top cover 66 of the disinfection chamber 50 may be made from aluminum or another heat-conducting metal. In this case, an external surface of the top cover may act as a passive heat sink, while the internal surface may act as both: (i) a heat sink surface exposed to active airflow inside the disinfection chamber 50, and (ii) as a reflective surface to redistribute UVC lights inside the chamber 50.

In further embodiments, heat-dissipating fins or round pins may be provided (i) on the outer surface of the top cover 64 for passive heat dissipation, and/or (ii) on the internal surface of the top cover 64 for active heat dissipation due to ongoing airflow throughout the disinfection chamber 50. In case the heat-dissipating elements are made as protruding inside the air disinfection chamber, they may be arranged to minimize the shaded areas inside the chamber 50, for example by positioning thereof radially away from the LED, so that one round pin is placed behind the other in a radial pattern minimizing obstruction of UVC rays emanating from the LED. In further embodiments, a guide rail 140 may be used as a large heat sink as described above in greater detail.

Outlet 54 of the disinfection chamber 50 may be operably connected to one or a series of nozzles or airflow openings arranged around the face of the user to create a suitable air curtain of disinfected air in front of the user's face.

The aft handling assembly may be equipped with a direct switch or a remotely controlled switch, such as through a smartphone app, for example, to allow the user to turn the device on or off as desired.

In embodiments, the controller may be equipped with visual (LED lights) or tactile indicators of remaining battery life. For example, about 10-15 min before battery depletion, a vibrating notification alert may be generated to alert the user to move away from the risk area as the operation time of the air handling unit comes to an end. Another way to communicate the low battery condition is to interrupt the airflow for a few seconds at a time. Pulsing airflow may be a signal to the user to warn about the low battery status.

In further embodiments, the controller of the air handling assembly may be configured to communicate wirelessly with an external device such as a smartphone of the user, for example using a Bluetooth module or a similar remote communication device. A low battery warning alert may be sent to the smartphone prompting the user to leave the high-risk area, plug in a portable power bank or attach a charging device, or put on a conventional mask if no alternative power source is available. Another advantage of such wireless communication is the ability to monitor the performance of the air sterilizer and alert the user when a periodically scheduled self-diagnostic check shows a failure.

The smartphone app may be used to upload software revisions and updates to the main controller or download usage or other data therefrom. Usage patterns may be used to optimize the battery life or for surveillance of product use in order to improve the design of future devices.

A further utility of having a smartphone app is to select between two or more modes of operation of the device, including:
  a. Normal mode adapted to provide about 10-15 l/min of airflow for regular operation,
  b. Extended Time mode, wherein the airflow may be reduced in predetermined increments, for example to 10 L/min or below. LEDs may be provided with reduced power as weal but sufficient to maintain a desired minimal disinfection dose. The advantage of this mode is extended battery time. This mode may be used in low risk areas where no people are observed in the vicinity of the user,
  c. Boost mode, where the airflow pump is operated to increase airflow up to 25-30 L/min, and LEDs are provided with more electrical power to assure delivery of safe disinfection dose of the UVC irradiation. This mode may be advantageous for performing physical exercises or in other circumstances where heavy breathing is expected. While this may reduce the operating time of the device, it may still provide for the unique capability of protecting the user during exercise, something conventional masks cannot achieve.

Other modes of operation may also be used, such as a normal or an increased efficacy of air disinfection. A normal efficacy may be selected to be corresponding to a predetermined log kill of the virus, for example, 2 log or 99%. Increased irradiation may be selected to temporarily raise the irradiation level to a higher kill ratio, for example, 3 log or 99.9%. This mode may be useful when a user enters a hospital or in other circumstances where virus contamination risk is higher than in everyday circumstances. Another possible mode is with reduced efficacy of disinfection, such as 1 log or 90% kill ratio, which may be used in a low-risk environment such as outdoors in order to conserve battery time.

In further embodiments, the operating mode with lower efficacy of irradiation may be changed automatically to the operating mode with higher efficacy of irradiation following a motion of lowering of the face shield, which presumably happens when the user is getting closer to other people. A switch back to a lower efficacy mode may be also automatically performed when a face shield is raised, which may be done in circumstances when the user leaves a company of other people.

The smartphone app may also be used to gradually increase or decrease the airflow and corresponding optical LED output so as to maintain safe disinfection of the air going through the disinfection chamber. Such gradual adjustment of the flow output of the device may be used to allow the user fine control of the device performance in accordance with the user preferences.

Finally, the ability to detect the location of the user using a GPS signal of the user's phone or an optional built-in GPS receiver associated with the device of the invention may be used to intelligently adjust the threshold of the minimum remaining time for the low battery alarm. For example, detecting the location of the user in close proximity to a safe area (such as a park or one's car) may be used to reduce the low battery threshold and allow the user to be present in a higher risk area longer—by knowing that it may not take much time for the user to reach a safe area upon depletion of the battery. However, if the user is detected to be located further away from a safe area, the low battery alarm may be activated sooner so as to allow ample time for the user to retrieve from such a high-risk area.

In further yet embodiments, at least some elements of the air sterilizer may be configured to be mounted elsewhere on the clothing of the user. In one example, a battery pack 170 may be mounted on a belt, placed in a pocket, or contain an optional clip for mounting elsewhere. A small size cable may be used to connect the power source with the rest of the air handling assembly.

In a further embodiment of the invention, the components of the device that are in direct contact with the user may be made disposable, while the disinfection chamber, the air pump, and the controller may be configured for multiple uses via detachable attachment to the disposable components of the device. This configuration may be especially useful for businesses to lend the device for their customers to assure their safety, such as for example for an airline to assure the safety of air travelers. After the device is used by an air traveler, the disposable portion of the device, such as a cap, head straps, or another type of headwear may be discarded and the remaining portion of the device may be cleaned, recharged, and prepared for the next passenger using a new cap. In a variation of the above, a disposable liner may be positioned to separate the air sterilizer from the skin and the head of the user. Such disposable liner may be changed after each customer so as to allow safe use of the device for multiple users.

The present invention may have a number of advantages over a conventional face mask:

The first product to allow full protection against all forms of the airborne virus, including aerosols Back to normal:
  Normal breathing
  Normal speaking, no muffled voice
  Normal eating
  Normal drinking
  Normal smiles and non-verbal communication
Works with a beard or other facial hair
Comfortable to wear
Keeps the face cool, no face sweating or irritation
No fogged glasses
Protects the eyes
No need to constantly adjust the facemask and put it over the nose
Easy to clean and reuse multiple times
Especially beneficial for extended use in situations with limited ventilation and close proximity to other people—airplanes, subways, buses, schools, elevators, movie theaters
Can be plugged in for indefinite performance time, such as for a cashier in a store
Protects the most vulnerable: elderly, people with preexisting conditions
Eco-friendly, rechargeable, no pollution from throwing masks away frequently
One size fits most, no need to trim or fit to size
Protects from other airborne pathogens including influenza (flu), SARS, tuberculosis, measles, chickenpox, viral pneumonia, etc.
Uniquely provides a personal safe air supply
Allows flexible use and adjustment of the level of protection as the situation around the user changes
Does not require extensive user training, facilitates intuitive operation
Reusable design configured for machine washing and self-disinfection
The face is always visible to others.

A method of protecting a user form airborne pathogen is provided with the steps of using the air sterilizer as described above, activating the air disinfection chamber to disinfect the ambient air flowing therethrough and if needed move the face shield to position thereof in front of the face of the user.

It is contemplated that any embodiment discussed in this specification can be implemented with respect to any method of the invention, and vice versa. It will be also understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. Incorporation by reference is limited such that no subject matter is incorporated that is contrary to the explicit disclosure herein, no claims included in the documents are incorporated by reference herein, and any definitions provided in the documents are not incorporated by reference herein unless expressly included herein.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, Aft AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12, 15, 20 or 25%.

All of the devices and/or methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

We claim:
1. An air sterilizer for everyday use to protect against an airborne pathogen, said air sterilizer comprising:
   a headwear item,
   a housing comprising an air disinfection chamber and an air pump enclosed therein and configured to cause ambient air to move through the disinfection chamber and then form an air curtain in front of a face of a user, wherein the air disinfection chamber is configured to inactivate or remove the airborne pathogen from the ambient air, and
   a face shield slidably mounted on the housing and configured to move partially or completely between a first position and a second position:
      i. the first position is characterized by the face shield retained over the headwear item with the housing positioned in a space formed between the face shield and the headwear item and above a visor extending outward from the headwear item, whereby the face shield is positioned above and away from the face of the user,
      ii. the second position is characterized by the face shield positioned below and in front of the headwear item, whereby the face shield is positioned in front of the face of the user.

2. The air sterilizer as in claim 1, wherein the housing is removably attached to the headwear item.

3. The air sterilizer as in claim 1, wherein the housing is configured to provide a curtain of ambient air emanating downwards from one or more openings in the visor, wherein the openings in the visor are operatively connected with the disinfection chamber.

4. The air sterilizer, as in claim 3, further comprising an arch-shaped guide rail mounted on the housing and extending from an outer edge of the visor toward a top of the headwear item, the face shield slidingly attached to the guide rail and configured to slide along thereof between the first position and the second position.

5. The air sterilizer as in claim 1, wherein the housing is detachably attached to the headwear item.

6. An air sterilizer for everyday use in an airborne pathogen-affected area, the air sterilizer comprising:
   a headwear item,
   a housing comprising an air disinfection chamber and an air pump configured to cause ambient air to move through the disinfection chamber and then form an air stream in front of the face of the user, the air disinfection chamber comprising at least one LED emitting ultraviolet light positioned to emit ultraviolet light within the disinfection chamber at a peak wavelength in a range from about 100 nm to about 290 nm, wherein the disinfection chamber is configured to create a tortuous airflow path, and wherein the disinfection chamber is configured to contain all ultraviolet light emitted by the at least one LED, and
   a face shield slidably mounted on the housing and configured to move and retained at any point between a first position away from a face of a user and a second position in front of the face of the user.

7. The air sterilizer as in claim 6 further comprising an arch-shaped guide rail mounted on the housing above the air disinfection chamber, the face shield slidingly attached to the guide rail and configured to slide along thereof between the first position and the second position.

8. The air sterilizer as in claim 7, wherein the at least one LED is attached to and is in thermal heat-transferring contact with the guide rail, the guide rail is positioned adjacent to the disinfection chamber and comprises at least one heat-dissipating fin and is made from a heat-conducting material, wherein the guide rail and configured to dissipate heat generated by the at least one LED.

9. The air sterilizer as in claim 6, wherein the air disinfection chamber comprises an inlet, an elongated airflow pathway, and an outlet, wherein the elongated airflow pathway has a length which is greater than a distance between the inlet and the outlet of the air disinfection chamber, and wherein the elongated airflow pathway is folded inside the air disinfection chamber, the at least one LED is centrally positioned inside the air disinfection chamber to illuminate the entire elongated airflow pathway and expose passing ambient air to ultraviolet irradiation emanated therefrom.

10. The air sterilizer as in claim 9, wherein the internal walls defining the elongated airflow pathway inside the air disinfection chamber are made from an ultraviolet light-transparent material so as to avoid shadow areas void of ultraviolet irradiation and maximize airflow exposure to ultraviolet irradiation emanated by the at least one LED.

11. The air sterilizer as in claim 9, wherein the at least one LED is operated to deliver at least 1 mJ/cm$^2$ of total ultraviolet irradiation to the air passing through the air disinfection chamber between the inlet and the outlet thereof.

12. The air sterilizer as in claim 11 further comprising a controller configured to operate the air pump and the at least one LED at different airflow speeds such as to maintain a minimum exposure of passing air to at least 1 mJ/cm$^2$ of ultraviolet irradiation at any of the airflow speeds by adjusting the intensity of the ultraviolet irradiation to follow an adjustment in airflow speed.

13. The air sterilizer as in claim 12, wherein the controller is operated using a smartphone application on a smartphone operatively and wirelessly connected to the controller.

14. The air sterilizer as in claim 12, wherein the minimal volume of disinfected air delivered by the air sterilizer is at least 3 l/min.

15. The air sterilizer as in claim 12, wherein the minimal volume of disinfected air delivered by the air sterilizer is at least 7 l/min.

16. The air sterilizer as in claim 6 further comprising a rechargeable battery mounted on the housing and configured to energize the at least one LED.

17. The air sterilizer as in claim 16, wherein the rechargeable battery is mounted on one side of the housing and the air handling assembly is mounted away from the rechargeable battery on another side of the housing, whereby distributing the weight of the air sterilizer for a balanced distribution thereof around the headwear item.

18. The air sterilizer as in claim 6, wherein the at least one LED is selected to emit ultraviolet light at a maximum wavelength in a range from 250 nm to 270 nm.

19. The air sterilizer as in claim 6, wherein internal surfaces of the air disinfection chamber defining a top, a bottom, and side walls thereof are made from or covered with a ultraviolet light reflective materials, thereby providing exposure of the passing ambient air to ultraviolet light reflected therefrom.

20. The air sterilizer as in claim 6, wherein an airflow path throughout the entire air sterilizer does not contain any air filter so as to minimize resistance of air passing therethrough.

* * * * *